Figure 1:
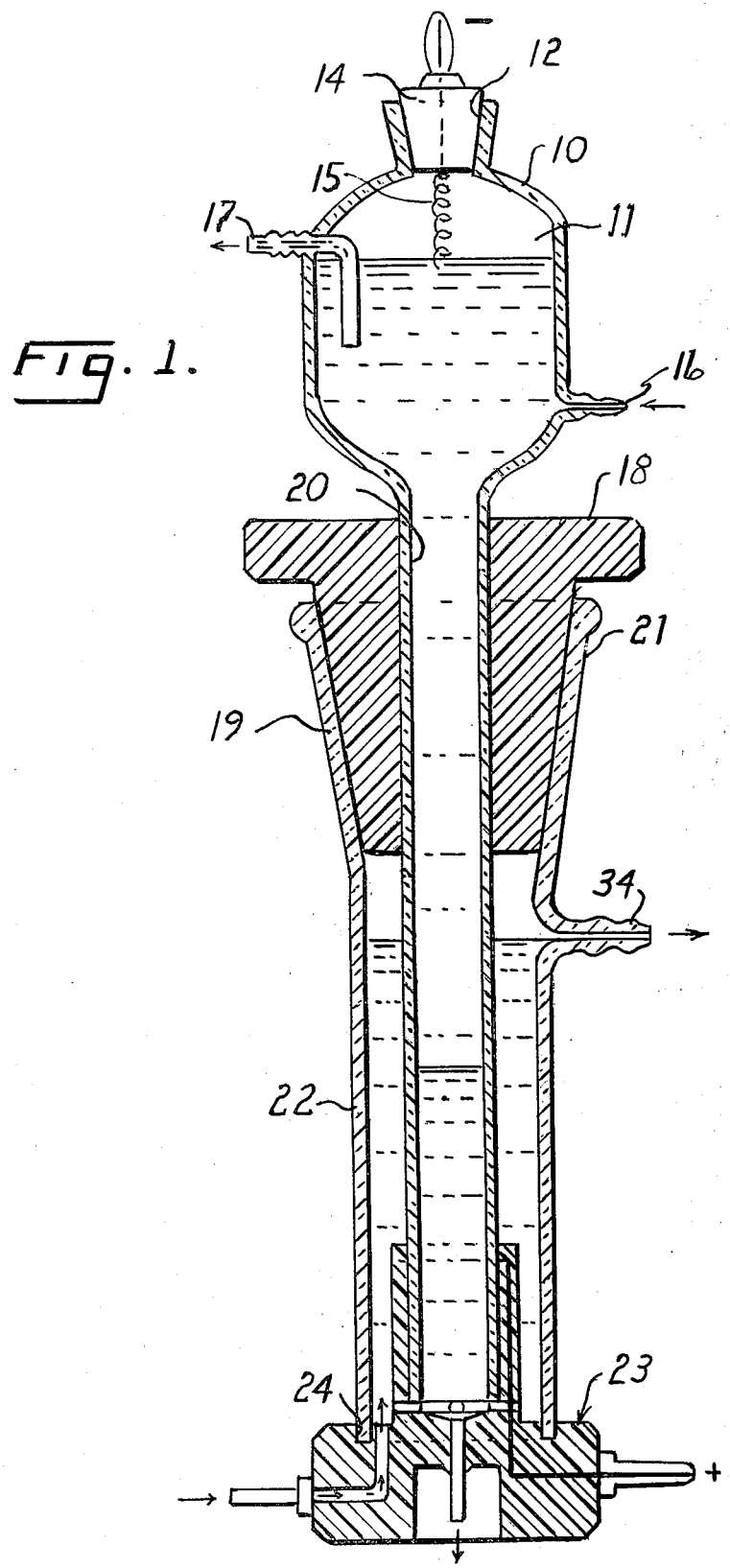

United States Patent
Caccavo

[11] 3,980,546
[45] Sept. 14, 1976

[54] MICROPREPARATIVE ELECTROPHORESIS APPARATUS

[76] Inventor: Francis A. Caccavo, 1984 W. 8 St., Brooklyn, N.Y. 11223

[22] Filed: June 27, 1975

[21] Appl. No.: 591,179

[52] U.S. Cl. .......................... 204/299 R; 204/180 G
[51] Int. Cl.² .................. G01N 27/26; G01N 27/28
[58] Field of Search ......................... 204/180 G; 299

[56] References Cited
UNITED STATES PATENTS

| | | | |
|---|---|---|---|
| 3,375,187 | 3/1968 | Buchler | 204/299 X |
| 3,453,200 | 7/1969 | Allington | 204/180 G X |
| 3,579,433 | 5/1971 | Dahlgren | 204/299 |
| 3,616,454 | 10/1971 | Levy et al. | 204/299 |
| 3,640,813 | 2/1972 | Nerenberg | 204/299 |
| 3,697,406 | 10/1972 | Svendsen | 204/180 G X |

*Primary Examiner*—John H. Mack
*Assistant Examiner*—A. C. Prescott
*Attorney, Agent, or Firm*—Howard T. Jeandron

[57] ABSTRACT

The Micropreparative electrophoresis apparatus comprises a first zone with an inlet and outlet for a buffer solution, a separation zone (gel column) an elution or collection zone, and a lower zone with an inlet and outlet for a buffer solution. To produce the electrophoresis there are two electrodes, one in the upper zone and the other in the lower zone, the electrodes being connected to a D.C. source of power. The first zone is partially filled with a gel or similar material and the shape of the zone is generally cylindrical. The electrical potential between the two electrodes and within the gel produces a separation of its layered components and therefore migration downward. The migration downward of the different components will be at different speeds. Migration is due to two factors, electrical charge of the particles being migrated with relation to the polarity of the electrodes, and molecular sieving action of the gel itself (porosity of gel). Thus the components leave the gel subsequently and thus enter the elution or collection zone where they are isolated, purified and subsequently collected in order of their separation. This apparatus provides a continuous collection according to the separation of the components within the gel and the speed of migration downward through the gel. This apparatus also provides a lower buffer chamber in which there is contained a gel column and elution chamber. The entire gel column is cooled as it migrates downward (A must for temperature sensitive materials).

4 Claims, 3 Drawing Figures

MICROPREPARATIVE ELECTROPHORESIS APPARATUS

There is a great variety or divergence in the construction and design of electrophoresis apparatuses, and particularly the elution chamber which fulfills several requirements. No dead space is permitted and a relatively low flow speed is necessary to insure minimum dilution of components. The flow rate used in eluting material out of the system is very slow, this is necessary in order not to dilute the components as they migrate off the column. In a microsystem only a few micrograms or at most a few milligrams of material is initially layered on top of the column. Thus as band separation occures we want to retrieve as much of these components undiluted or as little dilution as possible. A fast flow rate would give a considerable dilution. The design of the outlet is most important, it should be downward.

It is an object of this invention to provide a low flow speed of the buffer solution through the elution chamber to minimize dilution while transporting the migrated components out of the system.

It is a further object of this invention to provide a continuous electrolytic action through the gel during the downward movement of the components.

It is a still further object of this invention to provide a continuous collection of the separated components and a 100% recovery.

Figure 2:
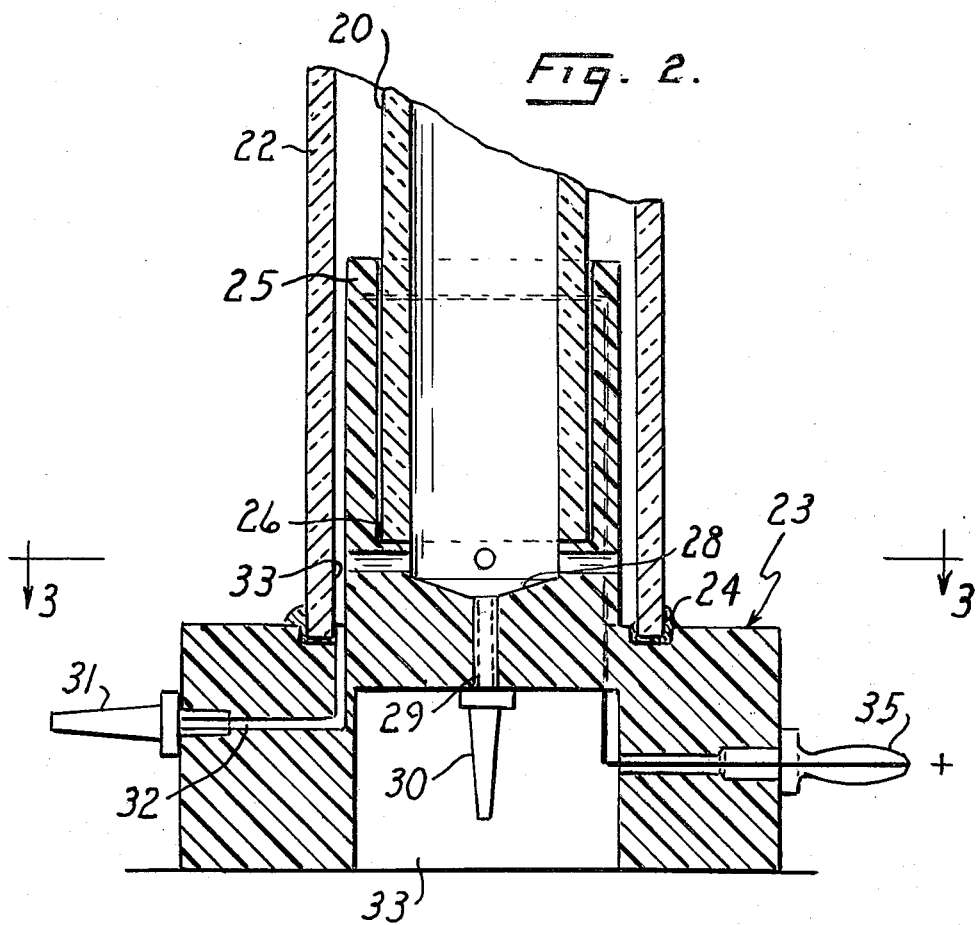
Figure 3:
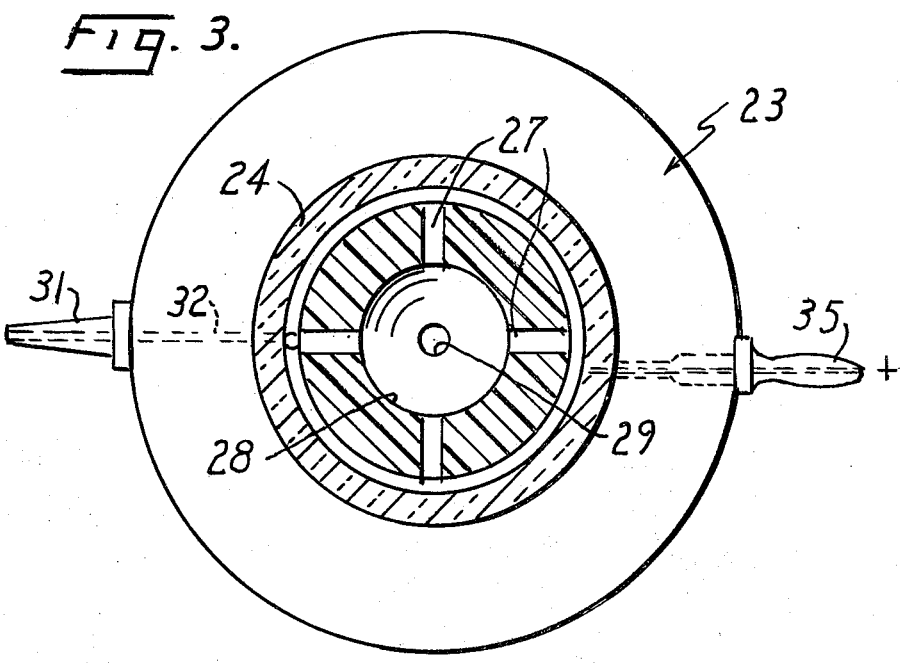

Other objects of this invention shall be apparent by reference to the accompanying detailed description and the drawings in which FIG. 1 is a cross sectional view of the microelectrophoresis apparatus, FIG. 2 is an enlarged view of the lower portion of FIG. 1 illustrating the elution chamber, and FIG. 3 is a cross sectional view taken on line 3—3 of FIG. 2.

Referring to the drawings and particularly FIG. 1 there is illustrated a complete micropreparative electrophoresis apparatus which comprises a first vessel 10 composed of glass and provided with a buffer chamber 11 at the upper end of the vessel with an extended circular tubelike migration area 20 through which the components will migrate during the electrophoresis in the gel. The vessel 10 is open with an aperture 12 at the top to permit inserting a plug 14, plug 14 having an electrode 15 inserted therethrough. Chamber 11 is provided with an inlet 16 and an outlet 17 for introduction and circulation of a buffer solution and overflow of the solution. The vessel 10 is provided with a plastic stopper shaped element 18, the element 18 having a central aperture through which the tubelike portion 20 passes so that element 18 can be fitted into a further vessel 19, vessel 19 having a funnel shaped top portion 21 and an extended neck portion 22 and the neck portion 22 fitted into a base or elution chamber 23 to form a complete apparatus.

Referring to FIGS. 2 and 3 the base 23 which constitutes an elution chamber which includes a circular depression 24 into which the tube 22 is fitted and sealed with epoxy in this relationship as illustrated in FIG. 2. Base 23 includes a raised portion 25 that fits within the tubular neck portion 22 with open area either side of portion 25 to allow the flow of a buffer solution. The raised portion 25 is of hollow construction having a central aperture into which the tubelike portion 20 is inserted and rests upon the base 23 at 26. Directly below the ridge 26 in the base 23 there are four ports 27 and the ports connect the exterior surface of the base with a central coneshaped aperture 28 and the center of the coneshaped aperture 28 is provided with an outlet port 29. For convenience a properly shaped insert 30 is mounted in 29 so that a tube can be connected over 30 for collecting the separated component flowing from the electrophoresis apparatus. There is also provided a similar insert 31 on the side of the base connected to a driller hole 32 that extends to the inner chamber 33 of the tubular neck portion 22. There is also provided an electrode 35 mounted through the base 23 and the electrode extending up through the base to the upper portion of 25 forming one electrode for the apparatus. And, referring to FIG. 1, the electrode 15 is the other electrode for the apparatus, both of these electrodes being conneced to a D.C. source (not shown) in the operation of the apparatus. It is to be noted that either electrode could be plus or minus depending upon attachment to D.C. power supply and way migration of material is to proceed.

It is to be noted that neck portion 22 is provided with an outlet 34 (FIG. 1) for the circulation of the lower buffer solution. Thus the circulated buffer solution also provides a cooling effect upon the tube 20 as the different components migrate down through the tube during the electrophoresis of these components. Referring to FIGS. 2 and 3 it is to be noted that the lower buffer solution circulation will produce a slicing effect upon the migrating components leaving tube 20 as well as a supporting effect on the migrating components in tube 20 thus eliminating the necessity for a membrane to contain the gel as normally used in many of the apparatuses of this type. The components that are migrating through the end of tube 20 and that are sliced or assisted in their movement downward by the buffer solution will fall into the coneshaped area 28 and pass through the outlet port 29 to be carried off as desired.

Although we have described the apparatus in detail it is understood that various modifications of the apparatus of the invention may be made without departing from the spirit of the scope thereof and this invention is limited only to the structure as defined in the appended claims.

What is claimed is:

1. A micropreparative electrophoresis apparatus, comprising
    a first vessel provided with an upper chamber with an inlet and outlet for the circulation of a buffer solution through said chamber, a downwardly extended tubular shaped portion for containing a gel during its downward migration and said tubular shaped portion open at its lower end, said first vessel provided with an inlet opening at the top of the upper chamber and a plug for said opening, an electrode extending through said plug, said downwardly extending tubular shaped portion provided with a stopper shaped element mounted in a tight sealed relationship about the exterior of said tube below said upper chamber
    a second vessel having a funnel shaped top to fit about the stopper and provide a seal, said second vessel generally tubular and extending downwardly approximately the same distance as the tubular portion of said first vessel,
    said tubular ends of said first vessel and second vessel abutting a base, said base provided with a circular depression on its upper surface to fit about the tubelike end of said second vessel and sealed in this relationship to form an elution chamber, said base also provided with a lesser radius raised hollow circular well like portion into which the tubular end of said first vessel fits and rests upon the surface of said base, said base hollowed out to form a coneshaped area below the tubular end of said first vessel and said coneshaped area connected to an outlet port under said base, said first vessel provided with a plurality of small ports about the periphery of the lower neck portion of the tubular end and said base provided with ports aligned with each of the lower neck ports, said base ports connected to the inner space between said tubular body portion of said first vessel and the tubular body of said second vessel, said inner space or chamber of said second vessel connected to an inlet port in said base and an outlet port situated well above said base, an electrode mounted in said base and extending up into the well like (elution) portion of said base, means to fill said tubular portion of said first vessel with a gel to be separated into its components, means to circulate a buffer solution through said first vessel and means to circulate a buffer solution through the lower end of the tubular portion of said second vessel and produce a cooling of the extended lower end of the first vessel and at the same time a D.C. circuit between the first and second vessels through the gel produces an electrophoresis and a migration of the components of the gel downward and means to support the gell column in the tubular portion of said first vessel with the lower buffer solution and means to slice off the lower end of the migrating components as they reach the bottom of their downward migration and collect the desired separated component.

2. An elution chamber comprising an upper tubular shaped portion adapted to be fitted to an electrophoresis gel column with said chamber open to the electrophoresis gel, said chamber further comprising a closed base with multiple laterally extending ports surrounding a centrally located, downwardly positioned exit aperture, said ports connecting said exit aperture with the exterior surface of said elution chamber, whereby the second buffer solution passes around said elution chamber and through said multiple ports to be in contact with an electrophoresis gel, slicing the migrating components leaving the gel.

3. In an apparatus according to claim 2 in which the elution chamber is adapted to circulate buffer so as to support the gel column.

4. In an apparatus according to claim 2 in which the lower circulating zone for the buffer solution surrounds the gel column in its downward migration and produces a cooling effect.

* * * * *